(12) United States Patent
Viswanathan et al.

(10) Patent No.: US 8,721,655 B2
(45) Date of Patent: May 13, 2014

(54) EFFICIENT CLOSED LOOP FEEDBACK NAVIGATION

(75) Inventors: Raju R. Viswanathan, St. Louis, MO (US); Walter M. Blume, Webster Groves, MO (US)

(73) Assignee: Stereotaxis, Inc., St. Louis, MO (US)

( * ) Notice: Subject to any disclaimer, the term of this patent is extended or adjusted under 35 U.S.C. 154(b) by 3060 days.

(21) Appl. No.: 10/879,694

(22) Filed: Jun. 29, 2004

(65) Prior Publication Data

US 2005/0020911 A1   Jan. 27, 2005

Related U.S. Application Data

(63) Continuation-in-part of application No. 10/844,056, filed on May 12, 2004, now abandoned, which is a continuation of application No. PCT/US03/10893, filed on Apr. 9, 2003.

(60) Provisional application No. 60/371,555, filed on Apr. 10, 2002.

(51) Int. Cl.
  *A61F 11/00*   (2006.01)

(52) U.S. Cl.
  USPC .......................................... 606/108; 606/130

(58) Field of Classification Search
  USPC ............. 434/239; 600/429, 12, 424; 606/108, 606/130; 604/95
  See application file for complete search history.

(56) References Cited

U.S. PATENT DOCUMENTS

| | | |
|---|---|---|
| 4,869,247 A | 9/1989 | Howard, III |
| 5,125,888 A | 6/1992 | Howard et al. |
| 6,015,414 A * | 1/2000 | Werp et al. ..................... 606/108 |
| 6,216,026 B1 | 4/2001 | Kuhn et al. |
| 6,298,257 B1 | 10/2001 | Hall et al. |
| 6,304,769 B1 | 10/2001 | Arenson et al. |
| 6,401,723 B1 | 6/2002 | Garibaldi et al. |
| 6,702,804 B1 * | 3/2004 | Ritter et al. ....................... 606/1 |
| 2002/0049375 A1 * | 4/2002 | Strommer et al. ............ 600/407 |

OTHER PUBLICATIONS

Lawton et al., "Ribbons and Groups: A thin rod theory for catheters and filaments" Journal of Physics A, vol. 32, No. 9, pp. 1709-1735 (1999).
Cheng et al., "Electrostrictive poly (vinylidene fluoride-trifluoroethylene) copolymers", App. Phys. Letter., vol. 74, pp. 1901-1903 (1999)—Revised under Sensors and Actuators A, vol. 90, pp. 138-147 (2001).
International Search Report and Written Opinion Dated: May 2, 2007 11 pages.

* cited by examiner

*Primary Examiner* — Elmer Chao
(74) *Attorney, Agent, or Firm* — Harness, Dickey & Pierce, P.L.C.

(57) ABSTRACT

The present invention provides a means for guiding a medical device within the body to approach a target destination. The system and method provide a means for determining a predicted length and orientation, navigating the device to an intermediate point less than the predicted length, determining an error between the projected destination and actual target destination, and successively updating a predicted value of a control variable to yield an orientation within a predetermined distance error before advancing the device the remaining distance to the destination. This provides a physician with the capability of verifying the device will be accurately guided to the target destination without trial and error. A method is also provided for intuitive navigation to targets with limited trial and error based on user-applied device orientation adjustments, where the user chooses the magnitude of the adjustments and the system determines the adjustment direction.

60 Claims, 10 Drawing Sheets

EFFICIENT CLOSED LOOP FEEDBACK NAVIGATION

CROSS REFERENCE TO RELATED APPLICATION

This application is a continuation of U.S. application Ser. No. 10/844,056, filed May 12, 2004, which is based on PCT Patent Application Ser. No. PCT/US03/10893, filed Apr. 9, 2003, which claims priority to U.S. Provisional Application Ser. No. 60/371,555, filed Apr. 10, 2002, all of which has been incorporated herein by reference.

FIELD OF THE INVENTION

This invention relates to a system and methods for interventional medicine, and more specifically to navigation of catheter and medical devices through the body to an operating region.

BACKGROUND OF THE INVENTION

Interventional medicine is the collection of medical procedures in which access to the site of treatment is made through one of the patient's blood vessels, body cavities or lumens. For example, angioplasty of a coronary artery is most often performed using a catheter which enters the patient's arterial system through a puncture of the femoral artery in the groin area. The procedure is referred to as PTCA, or Percutaneous (through the skin), Transluminal (through the blood vessel), Coronary (in the vessel of the heart), Angioplasty. Other interventional medical procedures include assessment and treatment of tissues on the inner surfaces of the heart (endocardial surfaces) accessed via peripheral veins or arteries, treatment of vascular defects such as cerebral aneurysms, removal of embolic clots and debris from vessels, treatment of tumors via vascular access, endoscopy of the intestinal tract, etc.

Interventional medicine technologies have been applied to manipulation of instruments which contact tissues during surgical procedures, making these procedures more precise, repeatable and less dependent of the device manipulation skills of the physician. Some presently available interventional medical systems for directing and manipulating the distal tip of a medical device by actuation of the distal portion of the device use computer assisted navigation and an imaging system for providing imaging of the device and blood vessels and tissues. Such systems can control the navigation of a medical device, such as a catheter, to a target destination in an operating region using a computer to orient and guide the distal tip through blood vessels and tissue. In some cases, when the computed direction for reaching the target destination is determined and the medical device is extended, the device tip may not reach the intended target exactly due to inaccuracies in the device or deviations in physical or geometric characteristics of the device from its ideal properties. A steering correction may be required to properly reorient the device to reach the intended target. To reach the target destination, a navigation system must accurately orient the device tip as it approaches the target before advancing the remaining distance to reach the given target. A method is therefore desired for controlling movement of a medical device approaching the target destination that will verify the device tip is being accurately guided to the intended destination before advancement, and will allow for accurate navigation in real time.

SUMMARY OF THE INVENTION

According to the principles of the present invention, a system and method are provided for control of a navigation system for deploying a catheter or medical device within the body in a manner such that a physician can input a target destination, and the navigation system will guide the catheter device within a short distance of the target and determine an orientation for the catheter tip that is within a predetermined error before advancing the catheter tip to the target destination. The present system and method provide a means for determining a predicted length and orientation, navigating the catheter device to an intermediate point less than the predicted length, determining an error between the projected destination and actual target destination, and successively updating a predicted value of a control variable to yield an orientation within a predetermined distance error before advancing the catheter device the remaining distance to the destination. A preferred embodiment of the present invention utilizes a magnetic navigation system that orients the distal end of a medical device in a selected direction through the interaction of magnetic fields associated with the medical device and one or more external source magnets outside the patient's body. The magnetic navigation system utilizes a field angle control variable for controlling the orientation direction of the medical device. The navigation system applies a magnetic field in a specific direction based on the field angle to orient the distal end of the medical device in the patent's body. An error of the predicted orientation and the actual orientation is determined by estimating the distance between a projected destination of the medical device if advanced in its current orientation and the desired target destination. The predicted orientation is iteratively updated and evaluated using a cost function until the distance error is within a predetermined minimum, to yield an optimum field angle that is applied to the catheter tip before advancing the catheter the remaining distance to the target destination. An estimation of the model response of predicted orientation relative to the field angle control variable may also be utilized to determine an updated field angle that will provide correction for variation in field direction, and will bring the actual orientation closer to the target destination. An updated field angle is determined and then applied, after which a new error and updated field angle are determined. This iterative process may be used to further correct the optimum angle to compensate for magnetic field variations, prior to advancing the catheter device to the intended target destination. The use of this method would provide the physician with the capability of verifying the medical device will be accurately guided to the target destination with only minimal or without any trial and error, to thereby reduce damage of the surrounding tissue.

In alternate embodiments, the actuation method could be based on mechanical, hydraulic, electrostrictive or other technologies known to those skilled in the art. The general scheme described here for device control is applicable to such other actuation methods as well. Thus while the methods taught herein detail the case of magnetic actuation for non-limiting illustrative purposes, the details can be adapted to other actuation techniques by those skilled in the art.

DETAILED DESCRIPTION OF THE INVENTION

Figure 1:
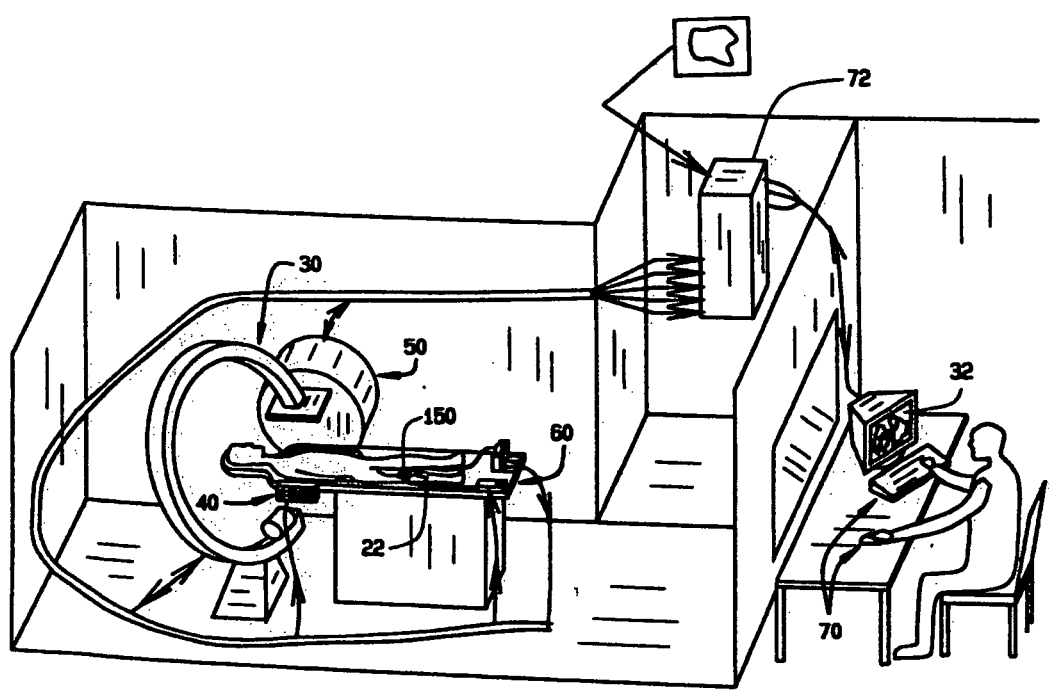
FIG. 1 is an illustration of an X-ray imaging system capable of providing images on at least two separate planes, together with an actuation system such as a magnetic field generator, for use in guiding a medical device through the lumens and cavities in the operating regions in a subject in accordance with the principles of this invention.

An automated system for navigating a medical device through the lumens and cavities in an operating region in a patient in accordance with the principles of this invention is indicated generally as 20 in FIG. 1. The system 20 comprises an elongate medical device 22, having a proximal end and a distal end adapted to be introduced into the operating region in a subject. The system 20 also comprises an imaging system 30 for displaying an image of the operating region on a display 32, including a representation of the distal end of the medical device 22 in the operating region.

The system also includes a navigation system for manipulating the distal end of the medical device 22. In this preferred embodiment the navigating system is a magnetic navigation system 50. Of course, the navigation system could alternatively be a piezoelectric system or a mechanical guide wire system or other suitable system for orienting the distal tip of the medical device. The magnetic navigation system 50 orients the distal end of the medical device 22 in a selected direction through the interaction of magnetic fields associated with the medical device 22 inside the operating region and at least one external source magnet outside the subject's body. The catheter may then be advanced in the selected direction, to reach the target destination through the successive reorientation stepwise process and advancement.

A preferred embodiment of the present invention describes a method for efficiently using real-time location information associated with an elongate flexible catheter or medical device provided by a localization system and controlling navigation in an automated or semi-automated manner to a desired target with the aid of a computer-controlled navigation system. The control or actuation means used to steer or navigate the medical device with computer controlled navigation system may be any of a variety of method known to those skilled in the art, such as mechanical, magnetic, electrostrictive, hydraulic, or others. One preferred embodiment is one where an externally applied magnetic field is used to steer the device, while device advancement and retraction is mechanically driven. Such a navigation system is typically used in conjunction with an X-ray system with a mutually known registration between the systems. Registration of coordinates between the localization system and the navigation system may be performed by placing suitable radio-opaque markers (at known locations in localization system coordinates) within the apparatus associated with the localization system, bringing these into the X-ray field of view, and fluoro-localizing these markers on the navigation system. Following this marker identification, a best-fit algorithm that attempts to match corresponding points employing a standard registration method such as the Procrustes method can be used to register the localization coordinate system with the navigation coordinate system. Alternatively, the catheter tip can be fluoro-localized and the localization system coordinates of the catheter tip can be suitably translated to match the fluoroscopy system coordinates of the catheter. If desired, orientation adjustment can also be included in the latter scheme.

Figure 4:
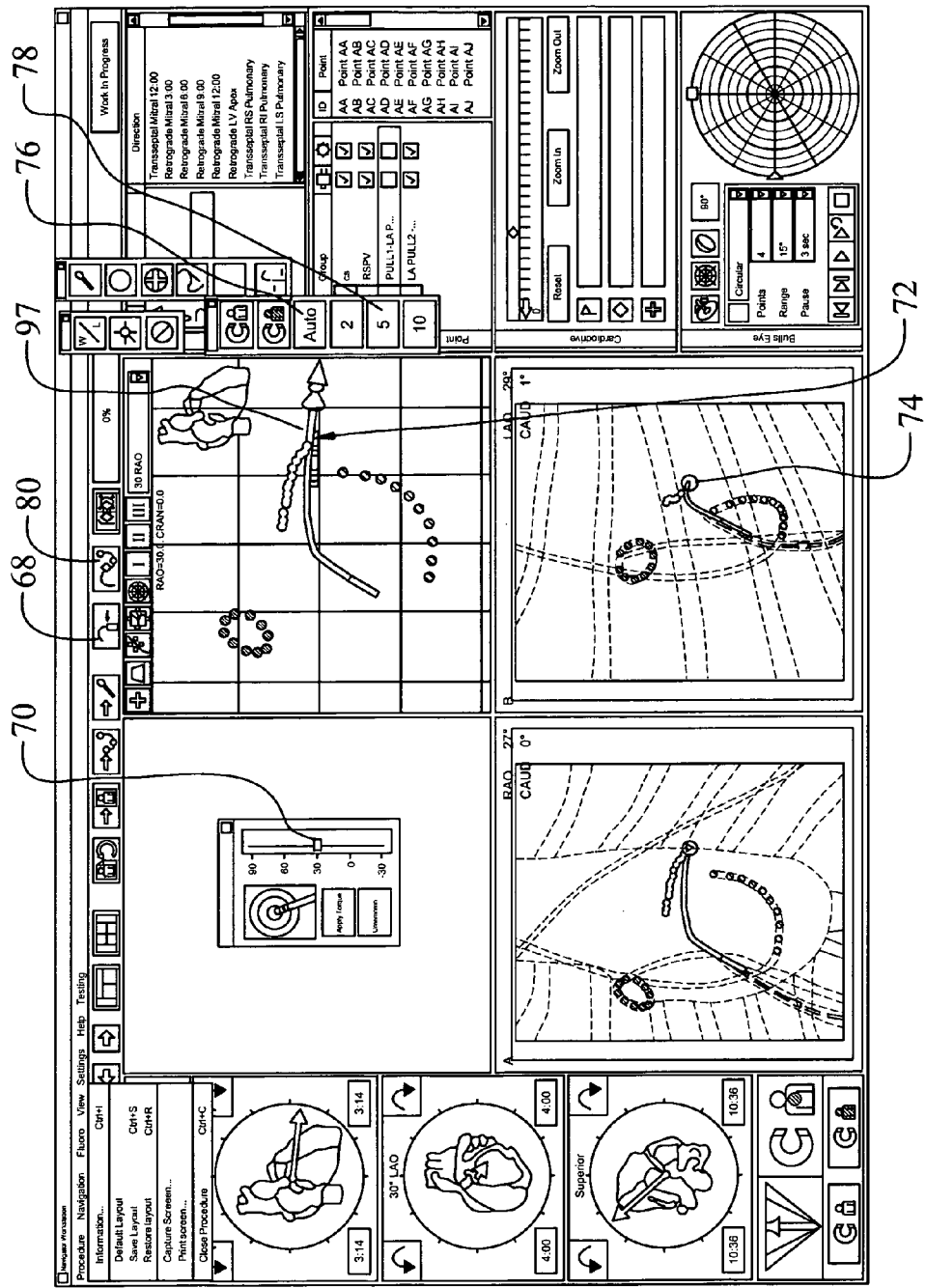
FIG. 4 is an illustration of a navigation system user interface displaying X-ray images from two separate planes, a series of points obtained from a localization system, a surface normal obtained from a localization system's map of an anatomical surface and a projection of the distal tip of a medical device localized from a localization system for use in guiding the medical device in a patient in accordance with the principles of this invention.

Given a three dimensional target location that is input from a user interface together with a pivot point and pivot orientation that defines a base support for the catheter device beyond which the device is extended and steered, a computational model of device response may be used to compute the magnetic field orientation and length of device ideally required to reach the target destination. The medical device is preferably deployed from the distal end of a relatively stiff sheath. The distal end of such a sheath functions as a base for the distal end of a medical device deployed therefrom. One efficient method to mark the pivot or base of the medical device is to position the catheter distal tip at the intended base, for example at the distal tip of a sheath, and then record the current real-time location and orientation (using a button as shown in FIG. 4 at 68) of the catheter tip as the pivot location and orientation. In some cases, however, when the computed field required to reach the target is applied and the device suitably extended beyond the base, the catheter tip may not reach the intended target exactly due to inaccuracies in device base information, deviations in physical or geometrical characteristics of the device away from its ideal properties, cardiac or anatomical motion, and such other factors. In such instances, one or more steering corrections can be applied to the device in order to account for changes in orientation due to length extension needed reach the intended target. Examples of the corrections that can be applied to the device are described below in one preferred embodiment.

Figure 6:
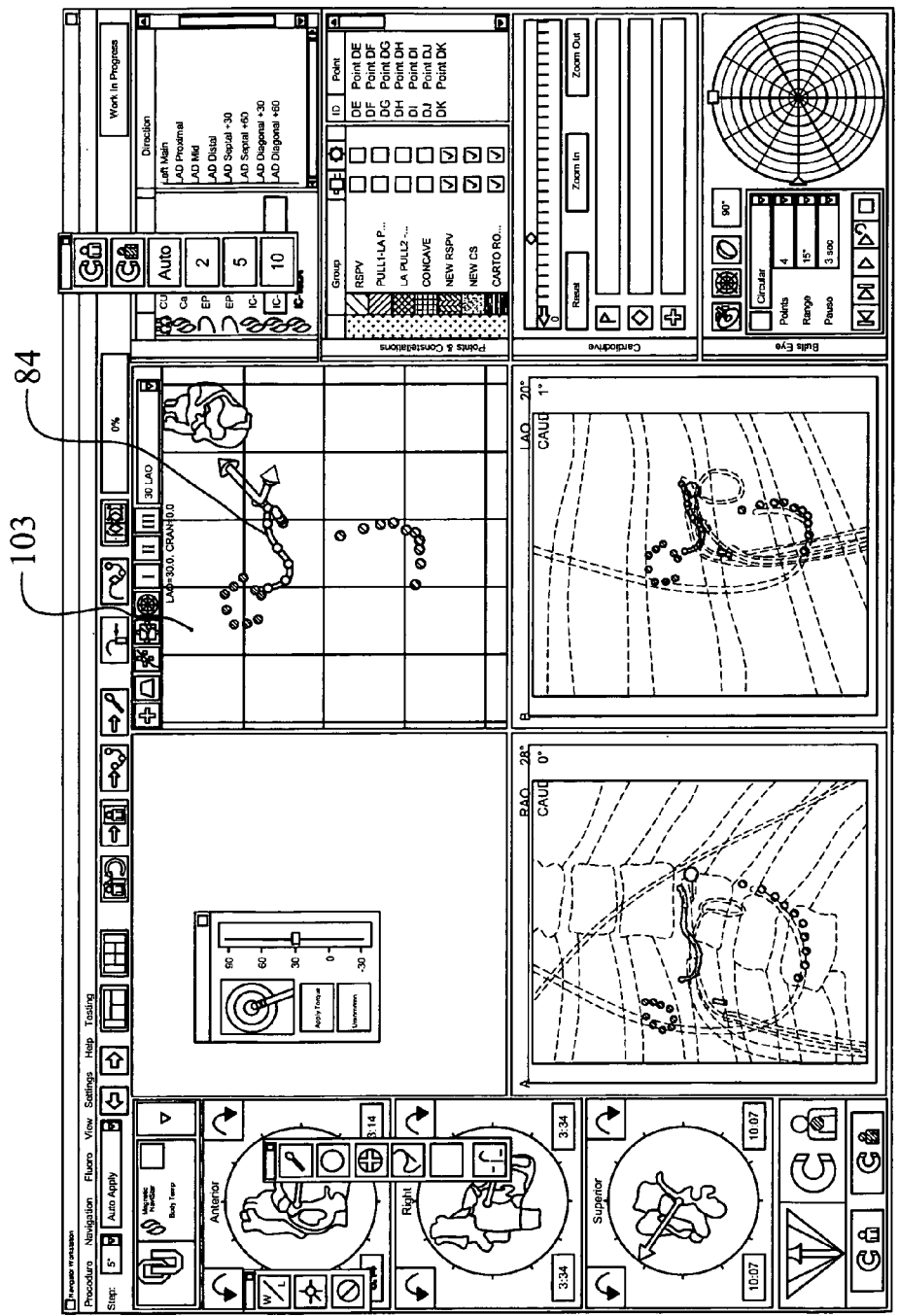
FIG. 6 is an illustration of a series of target destinations on the roof of a heart chamber to be ablated by the medical device that is guided by the system in accordance with the principles of this invention.

Following a suitable registration of the localization system (used to generate the real-time location information) to the navigation system, real-time catheter location and orientation information can be used to render the catheter in a graphical display which is either three dimensional or two dimensional such as in X-ray projections. The three dimensional window, labeled 103 in FIG. 6, is a display on the user interface of the navigation system wherein objects such as point locations, curves, surfaces, device shapes, device tip locations and various other objects of interest are graphically displayed in three dimensions, so that the entire set of objects in the display may be rotated and viewed from any orientation by suitable computer mouse movements. Likewise the entire three dimensional display can be scaled up or down to choose a desired level of zoom, most conveniently from a suitable use of the mouse. Such a display significantly aids the understanding of the spatial relationships between the objects of interest in the anatomy. In the case of X-ray images the device tip, suitably rendered graphically, can be overlaid or projected on at least one static X-ray image to visualize real-time device position, orientation and movement in an anatomical context, as shown in FIG. 4 at 74, while in the case of a three dimensional window in the user interface the localized device can be displayed within this window of the navigation system as shown by 72 in FIG. 4. By overlaying an updated display of the catheter over the X-ray images of the operating region, the graphical display provides a powerful means of visualizing the catheter in real time without the need for constantly updated fluoroscopic imaging, reducing the exposure to radiation of both physician and patient.

Figure 7:
FIG. 7 is an image showing the real-time location and orientation of a medical device displayed on a registered pre-operative three dimensional image of a heart.
Figure 8:
FIG. 8 is an image of a surface rendering of a heart, which could alternatively be used to display the real-time location and orientation of a medical device.

Likewise the real-time location and orientation of the device may be displayed (shown as 109 in FIG. 7) together with a registered pre-operative three dimensional image of the anatomy of interest (a heart is shown in FIG. 7 as an example), a surface rendering (FIG. 8) of the anatomy of interest, an intraoperative reconstruction of the anatomy of interest, or any other three dimensional reconstruction of the anatomy.

Figure 2:
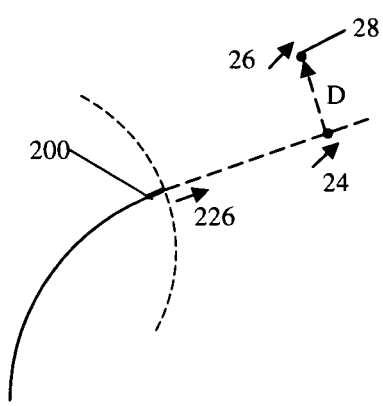
FIG. 2 is a diagram illustrating the approach of the tip of a medical device to a target destination, in accordance with the principles of this invention.

The navigation system and method of the present invention provide a means for accurately approaching a target destination in the operating region of a patent. First, after input of the target and the device base location and orientation, the present navigation system initially determines a predicted insertion length and orientation for deploying the catheter to the target destination, and advances the catheter a fraction of the predicted insertion length. In the preferred embodiment, this fraction is in the range of 0.75 to 0.95, but may alternatively be any fraction suitable for establishing an approach of the catheter tip 20 to the destination target 28 as shown in FIG. 2. The fraction can be fixed or it can be determined based on one or more variables. Next, the real-time location and orientation are used to determine whether the device tip is aimed directly at the target. If $\vec{x}_0$ is the current tip location, $\vec{x}_t$ is the target location, and $\vec{t}$ is the current tip orientation (unit) vector, the normal $\vec{n}'$ to the plane defined by the catheter tip orientation and the tip-to-target vector is $\vec{n}' = \lfloor \vec{t} \cdot (\vec{x}_t - \vec{x}_0) \rfloor$, which can be normalized by defining $\vec{n} = \vec{n}'/|\vec{n}'|$. If the magnitude of $\vec{n}'$ is small, then the tip orientation is closley aligned with the target and we are done. If not, a rotation about the unit normal $\vec{n}$ in a counterclockwise (m=+1) or clockwise (m=−1), with m defined as m=sign[(t×($x_T$−$x_0$)).n]) sense can be used to point the catheter tip directly at the target. While the extent of rotation is as yet undefined, in a semi-automated mode the user can make such rotational adjustments by trial and error in step-wise fashion until the real-time catheter tip can be seen to be aimed directly at the target in graphical displays on the user interface. The user does not need to specify the rotation axis, since this is computed by the navigation system; only a step size needs to be specified. In the case of a magnetic navigation system, a magnetic field rotation of an angle θ about n can be applied from suitable input buttons, in order to adjust the orientation of the device tip. Buttons can be provided with predetermined angle increments, which increments can dynamically change depending on the error or other factors.

In one preferred implementation of a semi-automated mode, small, medium and relatively large angular steps for θ, such as 2, 5 and 10 degrees respectively, are defined on the user interface by means of suitable graphical buttons as shown in FIG. 4 at 78. Such steps can be iteratively applied by the user until the catheter tip is seen to be aimed directly at the target in graphical displays on the user interface directly, whereupon the catheter can be advanced by a small amount in order to reach the target. During the course of this iterative user application of stepped moves, the above-described computation is repeatedly performed and applied.

In another preferred embodiment, the above manually applied process can be automated by means of a suitable graphical button as shown in FIG. 4 at 76. For example, the system can apply a sequence of small rotations, such as 2 degree steps, with the rotation axis repeatedly updated as described above, until the tip alignment with the desired target is satisfactory. A measure of tip alignment is provided by the perpendicular distance, or its squared value D, from the target to the line defined by the tip orientation vector t. This measure or cost function D is given mathematically by $$D = |(\vec{x}_t - \vec{x}_0) - \vec{t}[\vec{t} \cdot (\vec{x}_t - \vec{x}_0)]|^2 \qquad (1)$$

where the "." indicates a vector dot product. Once the tip alignment is satisfactory, the catheter or other device may be advanced a small amount in order to reach the target.

In another alternate embodiment, the automated method of aligning the catheter tip with the target can be considerably speeded up by the use of a rapidly converging algorithm based on cost function minimization. In this case convergence is mathematically guaranteed when adjustments are made in a single plane. The process can start with this plane defined by the initial catheter tip orientation and the tip-to-target vector. Where $\vec{n}_0$ is the corresponding unit normal as defined earlier, this embodiment defines:

$$\vec{y}_0 = \vec{x}_0 - \vec{n}_0[\vec{n}_0 \cdot (\vec{x}_0 - \vec{x}_t)] \qquad (2)$$

$$\vec{t}_p = [\vec{t} - \vec{n}_0(\vec{n}_0 \cdot \vec{t})]/|[\vec{t} - \vec{n}_0(\vec{n}_0 \cdot \vec{t})]| \qquad (3)$$

and the cost function $$E = |(\vec{x}_t - \vec{y}_0) - \vec{t}_p[\vec{t}_p \cdot (\vec{x}_t - \vec{y}_0)]|^2 \qquad (4)$$

Figure 3:
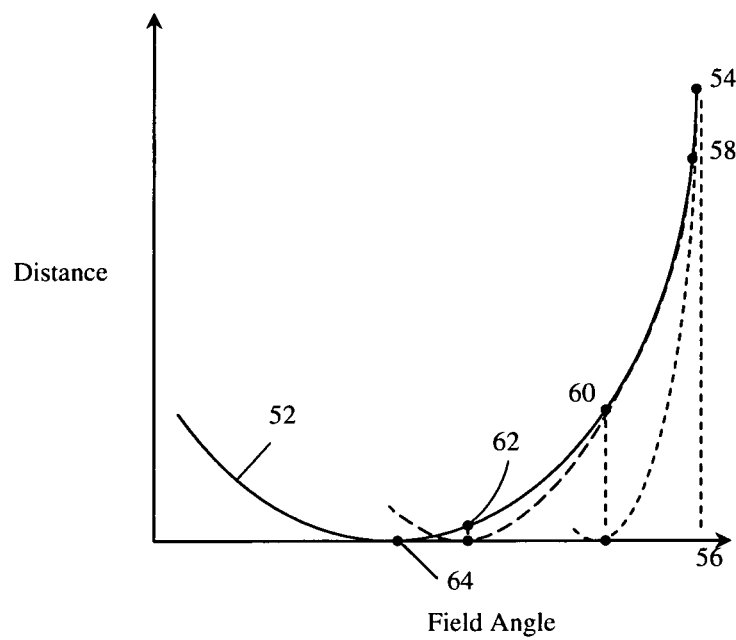
FIG. 3 is a graph illustrating the approach error of the tip of the medical device as the orientation angle of the tip of the device nears the optimum orientation for approaching the target destination.

The function E as a function of the control variable (in the case of magnetic navigation, the control variable is the magnetic field orientation) has a minimum of zero when the tip-to-target vector projected on the plane defined by $\vec{n}_0$ is aligned with (passes through) the target. Referring to FIG. 3, the squared distance E illustrated by the general curve 52 as a function of the field angle approaches zero at the optimum orientation. To obtain this orientation, the initial functional value $E_1$ shown as 54 is determined using equation (4) for the initial orientation angle, shown as 56 in FIG. 3, followed by an adjustment process. The adjustment process is based on a quadratic approximation of the behavior of the cost function and works as follows in the case of a magnetic navigation system, it being understood that a similar process may be constructed as well when any other means of actuation is used by the navigation system.

Starting from the initial position with a cost function of value $E_1$, an initial rotation of the magnetic field about $\vec{n}_0$ is made in a sense defined by $m_1 = \text{sign}\{[\vec{t}_p \cdot (\vec{x}_t - \vec{p}_1)] \cdot \vec{n}_0\}$ where $\vec{p}_1 = \vec{y}_0 + \vec{t}_p[\vec{t}_p \cdot (\vec{x}_t - \vec{y}_0)]$. This initial rotation is by an angular amount $\theta_2 \sim 10\text{-}30$ degrees. Define initially $\theta_1=0$. The catheter tip now moves to a new position and orientation, the tip location and orientation $\vec{x}_0$ and $\vec{t}$ are updated from the new real-time location data, and new quantities $m_2$ and $p_2$ are defined. The cost function correspondingly has a new value $E_2$., shown as 58 in FIG. 3.

The variable s can be defined as:

$$s = \text{sign}(m_1 m_2), \text{ and } q = s \cdot \left(\frac{E_2}{E_1}\right)^{1/2} \quad (5)$$

Also define
$$\theta^* = (\theta_2 - q\theta_1)/(1-q)$$

and then apply a field rotation of $(\theta^* - \theta_2)$. The values of $\theta_1$ and $\theta_2$ may be updated as: $\theta_1 \leftarrow \theta_2$, and $\theta_2 \leftarrow \theta^*$. The real-time catheter tip position and orientation, and the other quantities defined above including the cost function are also updated as $E_1 \leftarrow E_2$, followed by a freshly evaluated value of $E_2$. The process is repeated until the value of E as shown in FIG. 3 at points 60, 62 and 64 becomes sufficiently small, or alignment with the target is achieved in the plane defined by $\vec{n}_0$; in practice convergence can be achieved in a few iterations. In the preferred embodiment, the predetermined minimum error is preferably less than 4 mm$^2$ and is achieved in only a few iterations, but may alternatively be any value and any number of iterations that satisfies the level of accuracy desired.

In the general case, at the end of this process, the catheter may need a further adjustment in a second plane defined by the present unit normal $\vec{n}_f$ (defined by the catheter tip orientation and the tip-to-target vector); if so the entire process above can be repeated one or more times.

It can be shown mathematically that alignment with the target is certain at the completion of this step, at which point the catheter can be advanced the remainder of the distance until the target is reached.

In some cases the catheter device may deflect further by a small amount as it is advanced the remainder of the distance to the target. This can be corrected for by the use of a computational model of device behavior that quantifies this further variation in deflection. In the case of magnetic navigation, a linear dependence of catheter tip orientation changes on field direction changes for given lengths may be either pre-computed or calculated in real time, and this information can be used to apply a further correction of field orientation that will ensure the target is accurately reached. These corrections to be applied to the device are described below in one alternate embodiment.

Thus in an alternate embodiment of the present invention, a supplemental correction method may also be utilized to correct for variations in the magnetic field direction that may cause marginal orientation error during advancement of the final distance to the target destination. To correct for this error, the system uses a virtual model of the catheter, to determine the orientation $\theta_{m,1}$ of the tip of the model catheter, which may differ slightly from the actual orientation $\theta_{a,1}$. A model-based response coefficient is estimated as the ratio of the model orientation $\theta_{m,1}$ and the field angle $\theta_{f,1}$ with respect to the base of the catheter. Using this coefficient, a change in field angle to be applied to the tip of the catheter may be determined as shown below:

$$\Delta\theta_{f,1} = \frac{(\theta_{m,1} - \theta_{a,1})}{k_1}, \quad \text{where } k_1 = \frac{\theta_{m,1}}{\theta_{f,1}} \quad (6)$$

The navigation system may then apply the change in field angle and further advance the catheter a second fraction of the predicted length towards the target destination. The navigation system can compute the updated orientation $\theta_{m,2}$ of the tip of the model catheter, the updated actual orientation $\theta_{a,2}$ and a new model-based response coefficient $k_2$ from the ratio of the updated model orientation and the changed field angle resulting from the above equation (6). From the new response coefficient $k_2$, a new change in the field angle may be determined to apply a field correction. This method may be repeated as necessary to provide any level of correction accuracy desired.

Figure 5:
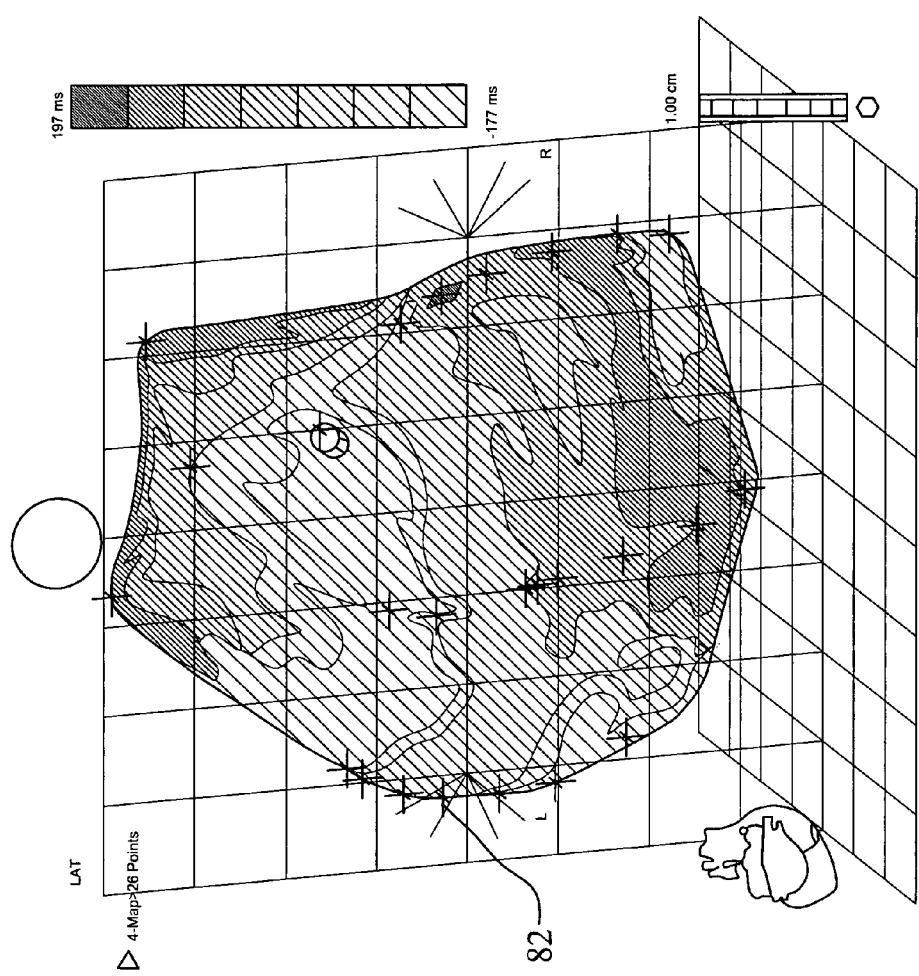
FIG. 5 is an illustration of a "drag" method of continuously acquiring a series of surface points by retracting a medical device in contact with a tissue surface while maintaining device deflection for good surface contact by suitable device actuation.
Figure 9A:
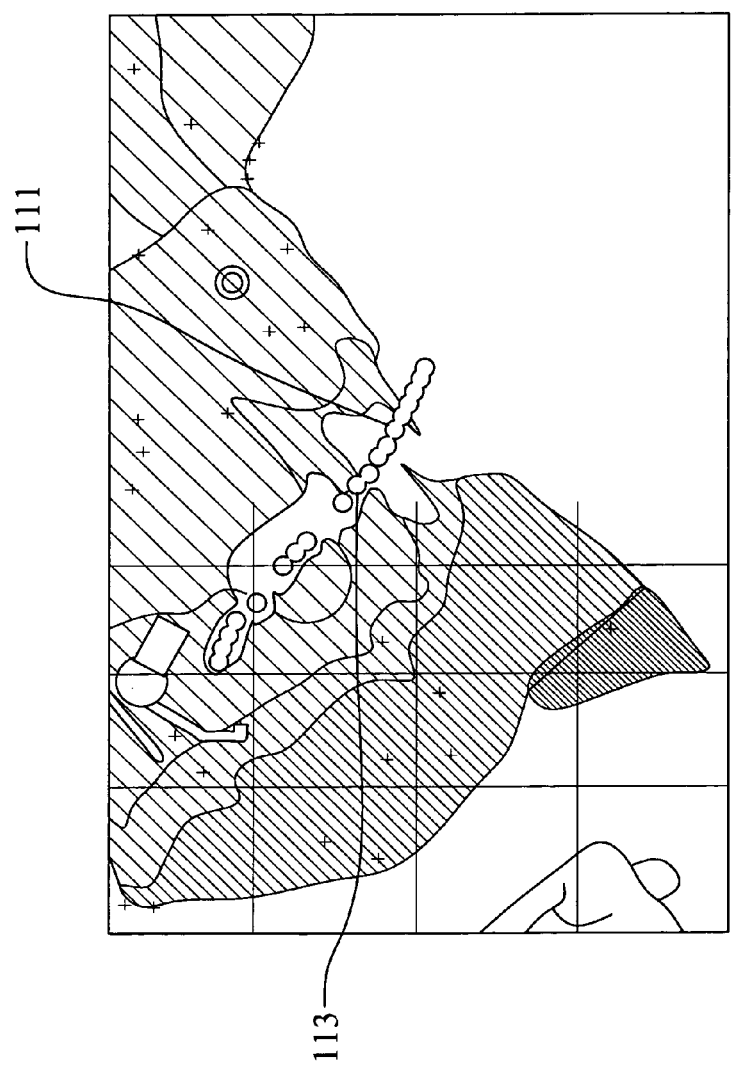
FIG. 9A is a an electrical activity surface rendering of an endocardial chamber, with gaps 111 in the surface where there was insufficient surface location data to permit closing the surface.
Figure 9B:
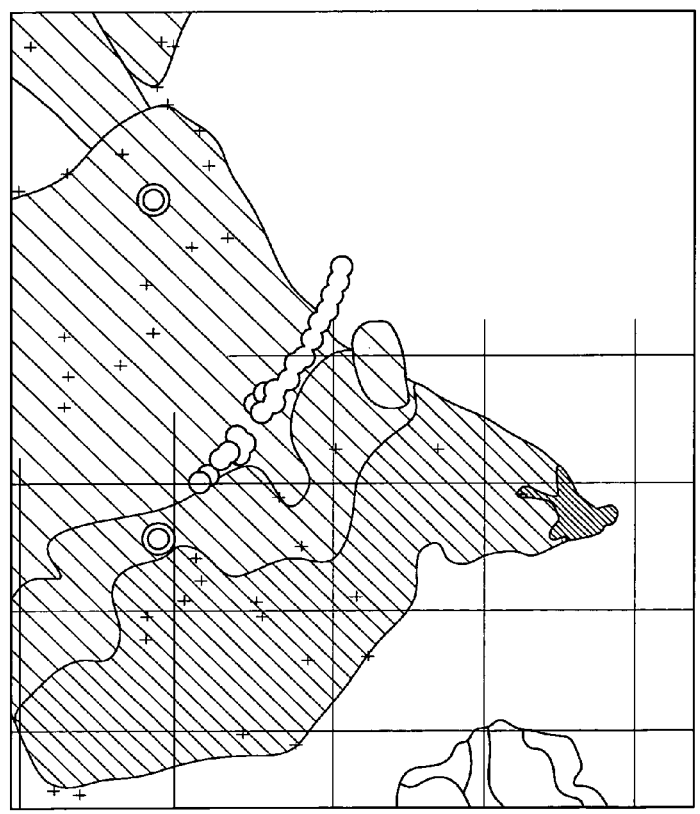
FIG. 9B is an an electrical activity surface rendering of an endocardial chamber, showing closure of the gaps shown in FIG. 9A.

Target locations and corresponding surface normals, or sets of target locations may be sent to the navigation system from a localization system for steering the catheter to these locations. In particular, when it is desired to explore or visit portions of the anatomy that have not been previously visited by the catheter, interpolated locations may be sent from a surface rendering on the localization system to the navigation system. The navigation system can steer the catheter to these interpolated locations and beyond if needed, thereby visiting more surface points to permit filling in data gaps and construction of a more refined anatomical surface rendering. The navigation system can steer the catheter in semi-automated or automated manner in order to make the creation of an anatomical map such as an electro-cardiogram or electrical activity map of heart tissue considerably more efficient than a manual trial and error method. FIG. 9A illustrates an electrical activity surface rendering of an endocardial chamber, with gaps 111 in the surface where there was insufficient surface location data to permit closing the surface. The navigation system can drive the device to approximately reach an interpolated set of locations 113 shown in FIG. 9A and locations recorded when a suitable Electro CardioGram signal is detected at the endocardial surface, thereby permitting closure of the surface gaps as illustrated in FIG. 9B. Likewise an idealized set of target locations, derived from an idealized three dimensional anatomical model, can also be used to make the mapping process more efficient. A drag method could also be used to defined a set of points used to make the mapping process more efficient, as shown in FIG. 5 at 82. While the field angle remains applied to over-torque the tip of the medical device into the tissue to establish contact, the device advancer may be retracted to drag the tip along the surface for enabling continuous acquisition of target points, which point locations may be suitably entered using a graphical button as shown in FIG. 4 at 80.

The real time device location data can also be used in cases where anatomical surface normal information is available to enhance contact of a medical device with tissue for purposes of maintaining a desired level of contact pressure, which is useful in the case of catheter ablation in electrophysiological applications. In cardiac applications when the device tip is within a use-specified distance from the target and good intracardiac electrical signals are maintained, a surface normal and device tip orientation vector may be defined. The surface normal information could be provided from three dimensional image data such as CT or MR data, or from an electrical activity surface rendering such as those provided by some localization systems such as the Carto system manufactured by Biosense-Webster Inc. An axis could then be defined by the cross product of the normal and orientation vector, and could be used to change the control variables driving device configuration in a such a manner as to increase tissue contact pressure. The amount of rotation can be controlled by an over-torque slider shown as 70 in FIG. 4, in an increased contact or decreased contact direction to provide an intuitive control of catheter contact, where all of the spatial computation of contact geometry is performed by the navigation system. The surface normal 97 at the target location, as obtained from the localization system and used in the computation of contact geometry, is also shown in FIG. 4. The use of a refined anatomical surface rendering could be used to determine a series of target points for ablation, such as on the inner surface of a heart chamber as shown in FIG. 6, along the line 84 comprising a series of target points.

The steering control of the medical device can be further augmented by the use of gated location data, for example where the gating is performed with respect to ECG (Electro CardioGraph) data, so that the device location is always measured at the same phase of a periodic cycle of anatomical motion such as the cardiac cycle. In a preferred embodiment, this data is input into the navigation system together with the real-time location data.

It should be noted that the advancement of the medical device could be manually controlled by a user input from an input device such as a joystick, or it could automatically be controlled by a computer. Alternatively, a joystick could also be used to control the advancement of the catheter device within a fractional amount of the length needed to approach the target destination, after which the system could orient the tip of the catheter to align with the target destination. Furthermore, a larger number of intermediate course corrections can also be applied if desired along the lines of the description given herein, in either semi-automated (with user-driven advancement) or automated fashion. Additional design considerations such as the above modifications may be made without departing from the spirit and scope of the invention. More particularly, the system and method may be adapted to medical device guidance systems other than magnetic navigation systems. Likewise, a variety of medical devices such as catheters, cannulas, guidewires, microcatheters, endoscopes and others known to those skilled in the art can be remotely guided according to the principles taught herein. Accordingly, it is not intended that the invention be limited by the particular form described above, but by the appended claims.

What is claimed:

1. A system for navigating the distal end of an elongate medical device in an operating region in a subject, the system comprising: an orientation system for remotely orienting the distal end of the medical device in a selected direction in the operating region; a movement system for controlling the length of the elongate medical device in the operating region; an input means of specifying a target destination point in the operating region; and a control means for achieving a predicted orientation of the device tip for reaching the target based on determining control variables, applying the control variables, positioning the device at a length less than that required to reach the target, making orientational adjustments of the device tip to correct the orientation error until the error is sufficiently small, and then advancing the device to the target.

2. A navigation system for navigating the distal end of an elongate medical device in an operating region in a subject, the system comprising: an orientation system for remotely orienting the distal end of the medical device in a selected direction in the operating region; a movement system for controlling the length of the elongate medical device; a control for: receiving an input of a destination point for the distal end of the elongate medical device in the operating region; operating the orientation system with a predicted value of at least one orientation system control variable to orient the distal tip to reach the destination point; operating the movement system to make the length of the elongate device less than the predicted length, to bring the distal end of the medical device to an intermediate point; while the length of the device remains substantially constant, successively (a) determining the error of the actual orientation of the device and (b) operating the orientation system with an updated predicted value of at least one orientation system control variable to orient the distal tip to reach the destination point; until the determined error is below a predetermined threshold; and thereafter operating the movement system to increase the length of the elongate medical device to bring the distal end of the device to the destination point.

3. The navigation system of claim 2, wherein the control applies an orientation correction to the device to account for change in orientation of the device due to the change in length needed to reach the target.

4. The navigation system according to claim 2 wherein the orientation system is a magnetic orientation system that applies a magnetic field in a specified direction to orient the distal end of the medical device, and wherein the at least one orientation system control variable is the direction of the applied magnetic field.

5. The navigation system according to claim 2 wherein the control uses data input from a localization system associated with the distal end of the medical device to determine the current position and orientation of the distal end of medical device, and wherein the control determines the error by determining the minimum distance between a projection from the distal end of the medical device in its current orientation and the destination point.

6. The navigation system of claim 5, wherein the control uses Electro-Cardiogram gating information and device location information in determining the error of the actual orientation of the device.

7. The navigation system of claim 5, further comprising a localization system and wherein the controller receives data input of target locations from the localization system.

8. The navigation system of claim 7, further comprising a display and wherein the localized device is graphically displayed to permit visual confirmation of target access.

9. The navigation system of claim 7, wherein navigation of the device to certain target locations within the body permits filling gaps in a map of an anatomical surface.

10. The navigation system of claim 5, wherein the control receives data inputs of targets on an anatomical surface and corresponding surface normals from a localization system, and uses the surface normal information and the device location and orientation information to compute an optimal change of at least one control variable in order to enhance device contact with the anatomical surface.

11. The navigation system of claim 5, wherein the control determines the real-time device location data at a place of mechanical support for the device at the proximal end is used as an identified input of device base data to the navigation system.

12. The navigation system of claim 5, wherein the control is configured to register localized device positional data obtained from the localization system to the navigation system coordinates.

13. The navigation system of claim 12, further comprising a connection to an X-ray system including an image display, and an image processor that graphically overlays the current location and orientation of the device on the image on the image display.

14. The navigation system of claim 13, wherein the current location and orientation of the device as determined by the localization system is suitably projected and corresponding graphics sent to the X-ray system for display on the live X-ray image display.

15. The navigation system of claim 5, wherein the current location and orientation of the device is graphically displayed in a three dimensional window display.

16. The navigation system of claim 5, wherein the current location and orientation of the device is graphically displayed together with a three dimensional preoperative image rendering.

17. The navigation system of claim 5, wherein the current location and orientation of the device is graphically displayed together with a surface rendering of a preoperative image.

18. The navigation system of claim 5, wherein the current location and orientation of the device is graphically displayed together with a three dimensional intra-operative image rendering.

19. The system according to claim 2, wherein the control operates the movement system to make the length of the elongate device less than the predicted length by operating the movement system to make the length of the medical device a predetermined fraction of the predicted length.

20. A system for navigating the distal end of an elongate medical device in an operating region in a subject, the system comprising: an orientation system for remotely orienting the distal end of the medical device in a selected direction in the operating region; a movement system for controlling the length of the elongate medical device; a control for: receiving an input of a destination point for the distal end of the elongate medical device in the operating region; determining a predicted value of at least one orientation system control variable to orient the distal tip to reach the destination point; predicting the length of control variable needed to reach the destination point; applying the predicted at least one orientation system control variable; operating the movement system to make the length of the elongate device less than the predicted length, to bring the distal end of the medical device to an intermediate point; until the determined error is below a predetermined threshold, determining an updated predicted a value of at least one orientation system control variable to orient the distal tip to reach the destination point; predicting the length of control variable reach the destination point; applying the updated predicted variable; and when the determined error is below the predetermined threshold, operating the movement system to increase the length of the elongate medical device to bring the distal end of the device to the destination point.

21. The system of claim 20, wherein the control applies an orientation correction to account for change in orientation of the device due to the change in length extension needed to reach the target.

22. The system according to claim 20, wherein the orientation system is a magnetic orientation system that applies a magnetic field in a specified direction to orient the distal end of the medical device, and wherein the at least one orientation system control variable is the direction of the applied magnetic field.

23. The system according to claim 20, wherein the control uses data input from a localization system associated with the distal end of the medical device to determine the current position and orientation of the distal end of medical device, and wherein the control determines the error by determining the minimum distance between a projection from a distal end of the medical device in its current orientation and the destination point.

24. The navigation system of claim 20, wherein the control uses real-time device location data at a place of mechanical support for the device is used as an identified input of device base data.

25. The navigation system of claim 20, wherein the control uses Electro-Cardiogram gating information and device location information in determining the error of the actual orientation of the device.

26. The navigation system of claim 20 further comprising a localization system and wherein the control receives data input of target locations from the localization system.

27. The navigation system of claim 26, further comprising a display, and wherein the localized device is graphically displayed on the display to permit visual confirmation of the target.

28. The navigation system of claim 27, wherein navigation of the device to some of the target locations therein permits filling gaps in a map of an anatomical surface.

29. The navigation system of claim 26, wherein the control receives data input of targets on an anatomical surface and corresponding surface normals from the localization system, wherein the surface normal information is used together with the device location and orientation to compute an optimal change of control variable in order to enhance device contact with the anatomical surface.

30. The system according to claim 20 wherein the control operates the movement system to make the length of the elongate device less than the predicted length by operating the movement system to make the length of the medical device a predetermined fraction of the predicted length.

31. The system according to claim 20 wherein the control operates the movement system to make the length of the elongate device less than the predicted length by operating the movement system to make the length of the medical device a predetermined amount shorter than the predicted length.

32. A method of controlling a navigation system comprising an orientation system for remotely orienting the distal end of the medical device in a selected direction in the operating region and a movement system for controlling the length of the elongate medical device in the operating region, to bring the distal end of an elongate medical device to a selected destination point, the method comprising: receiving an input of a destination point for the distal end of the elongate medical device in the operating region; operating the orientation system with a predicted value of at least one orientation system control variable to orient the distal tip to reach the destination point; operating the movement system to make the length of the elongate device less than the predicted length, to bring the distal end of the medical device to an intermediate point; while the length of the device remains substantially constant, successively (a) determining the error of the actual orientation of the device and (b) operating the orientation system with an updated predicted value of at least one orientation system control variable to orient the distal tip to reach the destination point until the determined error is below a predetermined threshold; and thereafter operating the movement system to increase the length of the elongate medical device to bring the distal end of the device to the destination point.

33. The method of claim 32, further comprising applying an orientation correction to the device to account for change in orientation of the device due to changing the length of the device to reach the target.

34. The method according to claim 32, wherein the orientation system is a magnetic orientation system that applies a magnetic field in a specified direction to orient the distal end of the medical device, and wherein the at least one orientation system control variable is the direction of the applied magnetic field.

35. The method according to claim 32, further comprising using data input from a localization system associated with the distal end of the medical device to determine the current position and orientation of the distal end of medical device, and wherein the step of determining the error comprises determining the minimum distance between a projection from the distal end of the medical device in its current orientation and the destination point.

36. The method of claim 35, further comprising using real-time device location data at a place of mechanical support for the device as an identified input of device base data.

37. The method of claim 35 further comprising using Electro-Cardiogram gating information and device location information in determining the error of the actual orientation information of the device.

38. The method of claim 35, further comprising receiving input of target locations from the localization system.

39. The method of claim 38, wherein a graphical display of the localized device is used to visually confirm target access.

40. The method of claim 38, wherein navigation of the device to some of the target locations therein permits filling gaps in a map of an anatomical surface.

41. The method of claim 35, further comprising using data input of targets on an anatomical surface and corresponding surface normals from the localization system, together with the device location and orientation to compute an optimal change of control variable in order to enhance device contact with the anatomical surface.

42. The method according to claim 35, wherein the step of operating the movement system to make the length of the elongate device less than the predicted length comprises operating the movement system to make the length of the medical device a predetermined fraction of the predicted length.

43. The method according to claim 32 wherein the step of operating the movement system to make the length of the elongate device less than the predicted length comprises operating the movement system to make the length of the medical device a predetermined fraction of the predicted length.

44. A method of controlling a navigation system comprising an orientation system for remotely orienting the distal end of the medical device in a selected direction in the operating region and a movement system for controlling the length of the elongate medical device in the operating region, to bring the distal end of an elongate medical device to a selected destination point, the method comprising: accepting an identification of a destination point in the operating region; determining at least one predicted control variable to orient the distal end of the medical device to reach the destination point; operating the movement system to adjust the length of the medical device to a length less than the length required to reach the destination point; operating the navigation system with the at least one predicted control variable; displaying graphically the current device tip location and orientation together with the destination point; automatically determining a direction of orientation adjustment required to align the device tip towards the destination point; and selecting and applying a magnitude of orientational adjustment in the determined adjustment direction.

45. The method according to claim 44 further comprising using data input from a localization system associated with the distal end of the medical device to determine the current position and orientation of the distal end of medical device.

46. The method according to claim 45, wherein the selection and application of a magnitude of orientational adjustment is repeated at least once.

47. The method of claim 45, wherein the movement system is subsequently operated to increase the length of the elongate medical device to bring the distal end of the device to the destination point.

48. The method of claim 47, further comprising applying an orientation correction to the device to account for change in orientation of the device due to the change in length needed to reach the target.

49. A method of controlling navigation system comprising an orientation system for remotely orienting the distal end of the medical device in a selected direction in the operating region and a movement system for controlling the length of the elongate medical device in the operating region, to bring the distal end of an elongate medical device to a selected destination point, the method comprising: receiving an input of a destination point for the distal end of the elongate medical device in the operating region; determining a predicted value of at least one orientation system control variable to orient the distal tip to reach the destination point; predicting the length of control variable reach the destination point; applying the predicted at least one orientation system control variable; operating the movement system to make the length of the elongate device less than the predicted length, to bring the distal end of the medical device to an intermediate point; until the determined error is below a predetermined threshold, determining an updated predicted value of at least one orientation system control variable to orient the distal tip to reach the destination point; applying the updated control variable; and when the determined error is below the predetermined threshold, operating the movement system to increase the length of the elongate medical device to bring the distal end of the device to the destination point.

50. The method of claim 49, further comprising applying an orientation correction to the device to account for change in orientation of the device due to the change in length needed to reach the target.

51. The method according to claim 50 wherein the orientation system is a magnetic orientation system that applies a magnetic field in a specified direction to orient the distal end of the medical device, and wherein the at least one orientation system control variable is the direction of the applied magnetic field.

52. The method according to claim 49 further comprising using data input from a localization system associated with the distal end of the medical device to determine the current position and orientation of the distal end of medical device, and wherein the step of determining the error comprises determining a function of the minimum distance between a projection from the distal end of the medical device in its current orientation and the destination point.

53. The method of claim 52, further comprising using real-time device location data at a place of mechanical support for the device as an identified input of device base data to the navigation system.

54. The method of claim 52 further comprising using Electro-Cardiogram gating information and device location information in determining the error of the actual orientation information of the device.

55. The method of claim 52, further comprising using data input of target locations from the localization system.

56. The method of claim 48, further comprising displaying the localized device on a display to permit visual confirmation of the target.

57. The method of claim 49, wherein navigation of the device to some of the target locations therein permits filling gaps in a map of an anatomical surface.

58. The method of claim 52, further comprising data input of targets on an anatomical surface and corresponding surface normals from the localization system, wherein the surface normal information is used together with the device location and orientation to compute an optimal change of control variable in order to enhance device contact with the anatomical surface.

59. The method according to claim 52 wherein the step of operating the movement system to make the length of the elongate device less than the predicted length comprises operating the movement system to make the length of the medical device a predetermined fraction of the predicted length.

60. The method according to claim 52 wherein the step of operating the movement system to make the length of the elongate device less than the predicted length comprises operating the movement system to make the length of the medical device a predetermined amount shorter than the predicted length.

\* \* \* \* \*